United States Patent [19]

Green et al.

[11] 4,433,690

[45] Feb. 28, 1984

[54] COMPACT ULTRASOUND APPARATUS FOR MEDICAL EXAMINATION

[75] Inventors: Philip S. Green, Atherton; Jon C. Taenzer, Palo Alto, both of Calif.

[73] Assignee: Siemens AG, Berlin and Munich, Fed. Rep. of Germany

[21] Appl. No.: 284,930

[22] Filed: Jul. 20, 1981

[51] Int. Cl.³ .............................................. A61B 10/00
[52] U.S. Cl. ...................................... 128/660; 73/642
[58] Field of Search .................. 128/660, 661, 642; 73/618-620, 624, 627-628, 631-632, 642, 644; 378/37, 177, 195-196, 208-209

[56] References Cited

U.S. PATENT DOCUMENTS

| | | | |
|---|---|---|---|
| 3,765,403 | 10/1973 | Brenden | 128/660 |
| 3,854,471 | 12/1974 | Wild | 128/660 |
| 3,937,066 | 2/1976 | Green et al. | |
| 3,959,770 | 5/1976 | Schaefer | 73/618 X |
| 3,963,933 | 6/1976 | Henkes, Jr. | 378/37 X |
| 3,991,316 | 11/1976 | Schmidt et al. | 378/37 |
| 4,001,766 | 1/1977 | Hurwitz | 73/642 X |
| 4,212,306 | 7/1980 | Mahmud | 128/665 |
| 4,252,125 | 2/1981 | Iinuma | |

OTHER PUBLICATIONS

Philip S. Green, "A New, High-Performance Ultrasonic Camera", *Acoustical Holography*, vol. 5, 1974, pp. 493-503.

J. R. Suarez et al., "Biomedical Imaging with the SRI Ultrasonic Camera", *Acoustical Holography*, vol. 6, pp. 1-13.

*Primary Examiner*—Kyle L. Howell
*Assistant Examiner*—Francis J. Jaworski
*Attorney, Agent, or Firm*—Karl F. Milde, Jr.

[57] ABSTRACT

The apparatus incorporates an ultrasonic wave-generating transducer for providing ultrasonic waves, a first and a second ultrasound window, a first guiding device for guiding the ultrasonic waves to the first window, an ultrasonic receiving transducer for transforming an acoustic image field received from the second window into electrical signals, and a second guiding device for guiding ultrasound transmitted through the second window to the receiving transducer. The ultrasound windows define an examination gap for insonifying a patient's organ positioned therein. The apparatus further incorporates a lens for focusing the acoustic image field received from the gap onto the receiving transducer. A mirror device, preferably a plane mirror, is associated with the second guiding device. This mirror deflects ultrasound energy that passes through the gap in a direction which is different from the main insonification direction in the gap. The second guiding device may comprise a compact scanning means for sweeping the acoustic image field across the receiving transducer.

14 Claims, 4 Drawing Figures

COMPACT ULTRASOUND APPARATUS FOR MEDICAL EXAMINATION

BACKGROUND OF THE INVENTION

1. Field of the Invention

This invention relates generally to an apparatus for generating an image according to an ultrasonic wave. In particular, this invention relates to an ultrasound apparatus for medical examinations of a patient. Still more particularly, this invention relates to an ultrasonic apparatus containing an ultrasonic wave generating transducer for providing ultrasonic waves to insonify an object under observation, and an ultrasonic receiving transducer for converting at least a portion of an acoustic image field received from the object to electrical signals.

2. Description of the Prior Art

Ultrasonic systems of the type herein contemplated are disclosed, for instance, in U.S. Pat. No. 3,937,066, in *Acoustical Holography*, Vol. 5, pages 493–503, 1974, and in *Acoustical Holography*, Vol. 6, pages 1–13, 1976.

In the ultrasonic systems according to the prior art, components such as the ultrasonic wave generating transducer, the focusing lens, the scanning device, and the ultrasonic receiving transducer are arranged on one axis. The prior art systems as a rule include as the scanning device a deflector assembly comprising a pair of acoustic prisms rotated in opposite rotational directions at the same speed. Due to the on-axis-arrangement, the whole system is usually very lengthy, and space problems may exist with respect to the arrangement in the examination room. Frequently a water tank is used between the emitting transducer and the receiving transducer. For examination purposes, the patient must enter the water tank. This is inconvenient especially for elderly patients. In addition, the prior art ultrasound systems generally do not provide for any clearance for non-observed organs of the patient. Therefore, especially breast examinations are difficult to perform. Also, in a typical prior art ultrasonic system examinations of the breast in different directions are only possible if the patient herself moves into various positions. The system itself is stationary so that precise directional examinations are difficult to make.

SUMMARY OF THE INVENTION

Objects

It is an object of this invention to provide a compact ultrasound apparatus for medical examinations of a patient.

It is another object of this invention to provide an ultrasonic apparatus for medical examinations of a patient who does not have to be immersed into a tank filled with a liquid such as water.

It is still another object of this invention to provide an ultrasonic apparatus for medical examinations of a patient which apparatus is provided with free space or clearances for parts or organs of the human body which are not under examination.

It is still another object of this invention to provide an ultrasonic apparatus for medical examinations of a patient which apparatus is adjustable to the thickness of the organ under examination.

It is still another object of this invention to provide an apparatus particularly suitable for routine examinations of the female breast.

It is still another object of this invention to provide an ultrasound apparatus which can easily be used for examinations of a human organ such as the female breast in various directions.

Summary

According to this invention, an ultrasound apparatus for medical examinations of a patient incorporates an ultrasonic wave generating transducer for providing ultrasonic waves. The apparatus also incorporates a first and a second ultrasound window. A first guiding device containing a fluid medium is provided for guiding the ultrasonic waves from the transducer to the first window. The first and the second ultrasound windows define an examination space or gap for introducing therewithin and insonifying a patient's organ. In the gap the ultrasound travels along a main insonification direction. The apparatus also incorporates an ultrasonic receiving transducer for converting at least a portion of an acoustic image field received from the examination gap to electric signals. A second guiding device also containing a fluid medium is provided for guiding the ultrasound which is transmitted through the gap from the second window to the ultrasound receiving transducer. A lens or a lens system is associated with the second guiding device. It is provided for focusing the acoustic image field from the gap at the ultrasonic receiving transducer and for forming an image of the patient's organ. The ultrasonic apparatus also contains a deflecting device such as a flat mirror associated with the second guiding device for deflecting ultrasound energy which passes through the gap towards the receiving transducer in a direction which is different from the main insonification direction of the gap. Thus, the acoustic axis of the apparatus is folded by the deflecting device.

The ultrasound apparatus may further comprise a sweeping or scanning device for sweeping the acoustic image field across the receiving transducer. This transducer preferably contains a certain number of elongated piezoelectric sensor elements. The sweeping device is arranged in that portion of the ultrasound path which is defined by the second guiding device, that is between the gap and the receiving transducer. In particular, the sweeping device may comprise a mirror which is moveable forth and back about a rotation axis. Such a design including a rocking mirror is especially compact.

The ultrasound apparatus may preferably be designed such that the gap may be pivoted about an axis. For instance, for breast examinations the gap may be rotated about a horizontal axis. In such a design examinations of the breast from various directions are possible.

The foregoing and other objects, features and advantages of the invention will be apparent from the following more particular description of preferred embodiments of the invention, as illustrated in the accompanying drawings.

DESCRIPTION OF THE PREFERRED EMBODIMENTS

Figure 1:
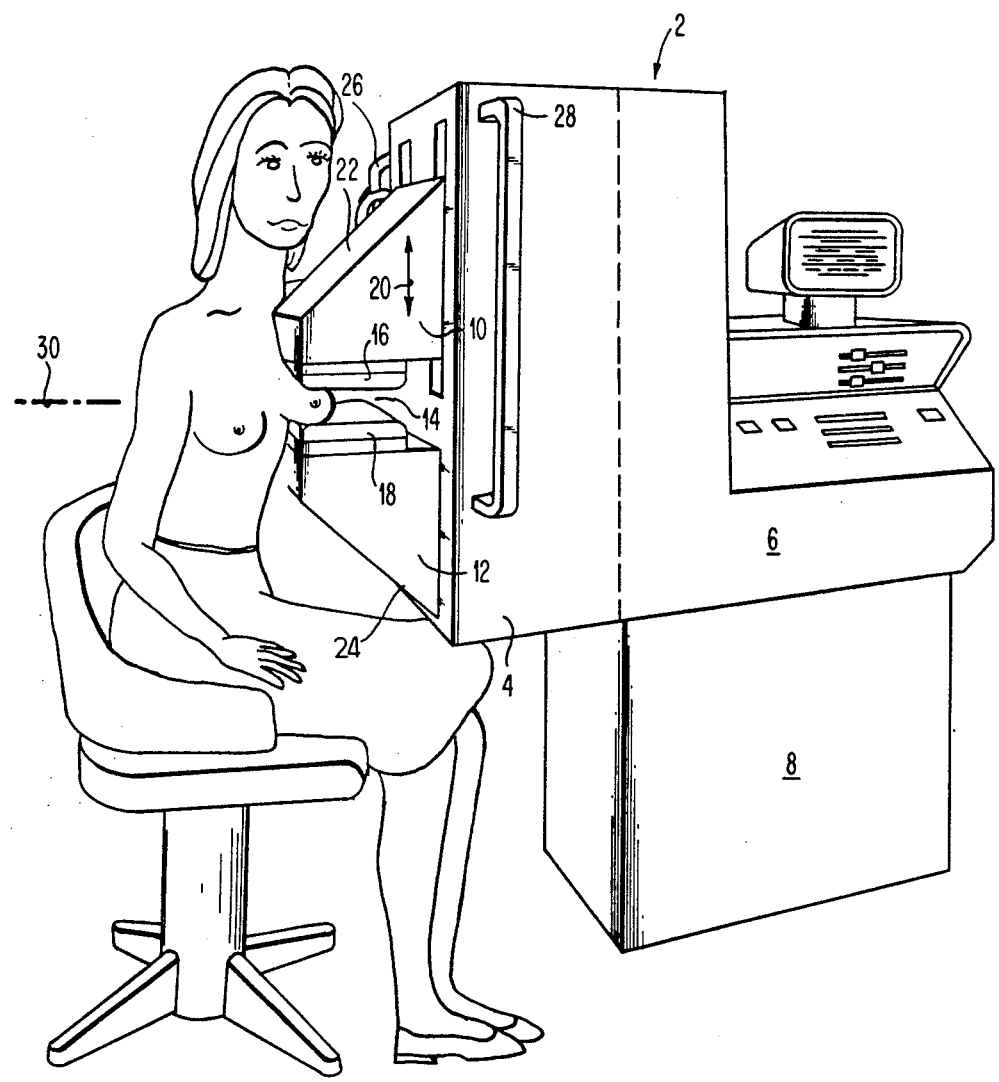
FIG. 1 is an overall perspective view of an embodiment of an ultrasonic transmission imaging system according to this invention.

With reference to FIG. 1, a patient is sitting upright on a chair in front of an ultrasonic transmission imaging system or ultrasound examination apparatus 2. The ultrasound apparatus 2 comprises a front portion 4 and a back portion 6 which is supported by a pedestal 8. The front portion 4 supports on its front side two protruding housing compartments 10 and 12. Both compartments 10 and 12 are provided for housing components and parts for generating, transmitting and/or receiving ultrasound waves. The sides of these compartments 10 and 12 that face each other are provided with ultrasonically transparent windows forming a free space or an examination gap 14 therebetween. Each ultrasound window may be provided with a pillow or soft resting pad 16 and 18, respectively, which are filled with a coupling liquid.

As illustrated in FIG. 1 the patient's breast is positioned in the examination gap 14 between the ultrasound windows. Ultrasound waves are applied in a vertical direction. The upper compartment 10 is vertically adjustable so as to provide gentle compression to the organ or as here discussed the breast of the patient. Thus the breast is slightly deformed to provide upper and lower substantially parallel surfaces. It has been found that good examination results can be achieved if all parts of the organ under examination have approximately the same thickness. The possibility of adjusting the examination space 14 is indicated in FIG. 1 by a double arrow 20.

As can be seen in FIG. 1, the upper compartment 10 has a sloping upper end face 22, and the lower compartment 12 has a sloping lower end face 24. These sloping end faces 22 and 24 leave free space for the patient's upper and lower body portions.

For the convenience of the patient, the front portion 4 is provided with side handles 26 and 28. These side handles 26 and 28 extend in a vertical direction.

The front portion 4 of the ultrasound apparatus 2 may be pivoted about a horizontal axis 30. For this purpose the front portion 4 is rotatably mounted on the back portion 6 by means of a horizontal pivot axis 32 as indicated at the right side of FIG. 2. Rotation about the horizontal axis 30 passing preferably through the examination gap 14 make examinations of the breast in various directions possible.

Figure 2:
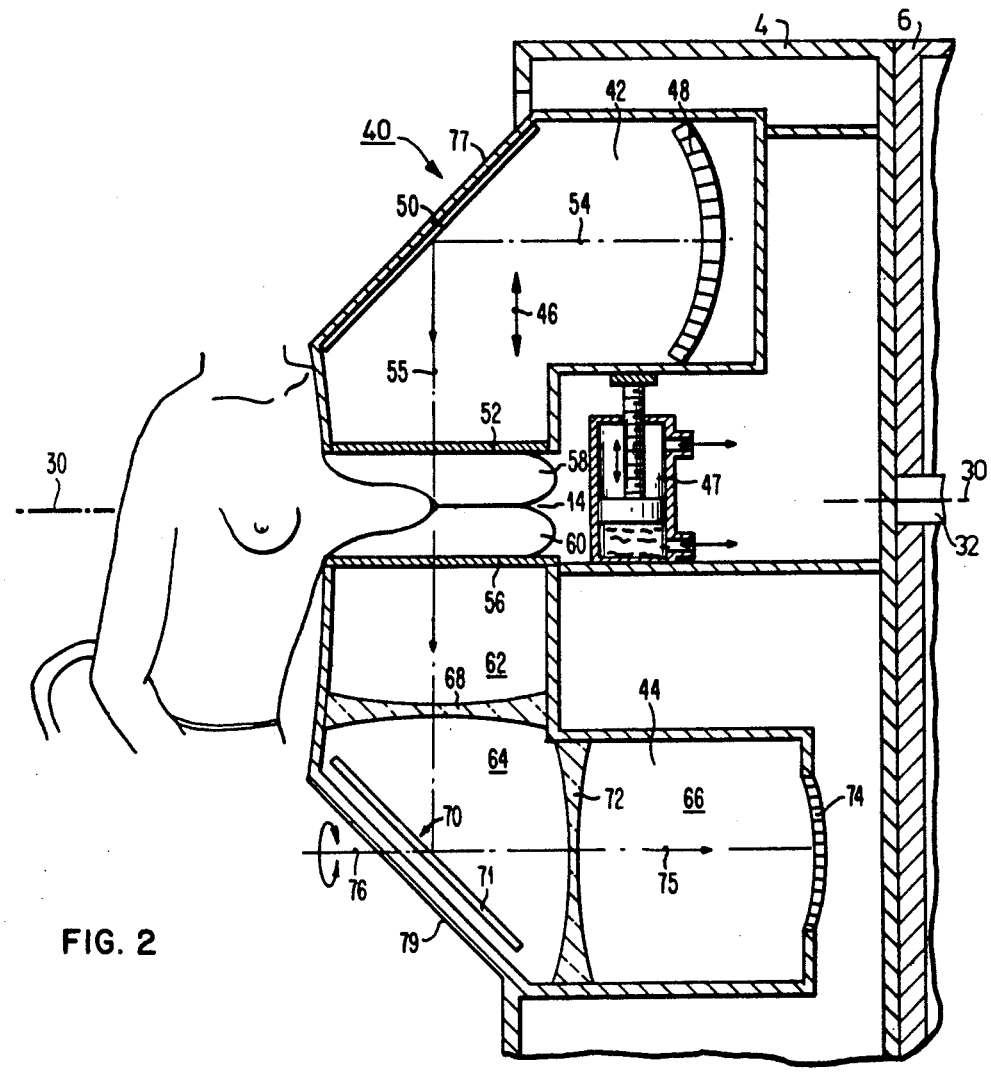
FIG. 2 is a cross-sectional view of the ultrasonic transmission imaging system, said system including a compact scanning device for ultrasound.

In FIG. 2 a view of an embodiment of an ultrasonic transmission imaging apparatus is illustrated, primarily in cross section. The electronic system for generating and evaluating electronic signals is not shown. In particular, the illustrated apparatus 40 is a transmission C-scan breast scanner. The illustrated apparatus 40 makes use of folding the acoustic main axis twice. Therefore, the instrument's bulk in regions close to the breast of the patient can be kept small.

The ultrasound apparatus 40 illustrated in FIG. 2 comprises two units, that is an ultrasonic transmitting unit 42 with a tissue coupling element, and an ultrasonic receiving unit 44 with a similar coupling element. The transmitting unit 42 is mounted over the receiving unit 44.

The ultrasonic transmitting unit 42 is housed in a separate compartment. It is vertically movable, as illustrated by the double arrow 46, in any well known manner in order to make the ultrasound apparatus 40 adjustable for patient access. A pneumatic or hydraulic cylinder 47 may be used for performing such movement. Also other driving means may be applied, such as an electric motor in combination with a gear mechanism and/or a lead screw. The transmitting unit 42 contains an ultrasonic wave generating transducer 48 for providing ultrasonic waves. A transducer 48 which contains a curved array of transmitting transducer elements is well-known in the art. The transmitting unit 42 also contains a mirror 50 for deflecting ultrasonic waves emitted from the transducer 48 towards a first ultrasound window 52. The mirror 50 is positioned at an angle of 45° with respect to the horizontal main axis 54 of the ultrasonic waves. Thus, it provides for a deflection by 90°. The main axis 55 is now positioned vertically. The first ultrasound window 52 contains an ultrasonically transparent rigid plate. The interior of the transmitting unit 42 is filled with a matching fluid medium such as water.

The ultrasonic receiving unit 44 is provided on its upper end with a second ultrasound window 56. The first window 52 and the second window 56 define an examination gap 14 for introducing and insonifying a patient's breast. The second window 56 is also an ultrasonically transparent rigid plate. Besides the rigid plates, the two ultrasound windows 52 and 56 may also comprise soft resting pads 58 and 60, respectively, filled with a matching fluid such as water. The pads 58 and 60 provide compression of the tissue and unimpeded ultrasonic transmission. It may also be desirable, however, that in routine breast examinations the pads 58 and 60 be omitted so as to provide smooth planar surfaces of the upper and lower windows 52 and 56 to compress the breast to an even thickness.

The receiving unit 44 contains three ultrasound propagation chambers 62, 64 and 66. The first and third chambers 62 and 66 are filled with a tissue-velocity matching liquid, as water for instance. Interposed between these chambers 62 and 66 is the second chamber 64 which represents a focusing and deflecting unit. This unit contains a first ultrasonic imaging lens 68 of a solid material, a scanning or sweeping device 70, and a second ultrasonic imaging lens 72 of a solid material. The scanning device 70 is used to sweep ultrasonic waves received from the second window 56 across a receiving transducer array 74 arranged at the rear of the chamber 66. The chamber 64 containing the focusing and deflecting unit is filled with a liquid (e.g. fluoridated hydrocarbon) having an ultrasound velocity lower than that of water. The liquid provides improved focusing properties. The receiving transducer array 74 preferably is a well-known curved array of elongated piezoelectric detector elements.

In particular, a vibrating or rocking mirror 71 is used as the sweeping device 70 for deflecting the ultrasonic waves. In its resting position, the rocking mirror is arranged at a suitable angle such as 45° with respect to the main axis 55 of the ultrasound waves received from the second window 56. Thus, it provides for a folding of the ultrasonic path e.g. by 90°. In the embodiment of FIG. 2, the main axis 75 is positioned horizontally. The mirror 71 may be vibrated about a vertical or a horizontal axis, thereby sweeping the ultrasound waves across the receiving transducer array 74 at the rear of the water-filled chamber 66. The low velocity-of-sound-propagation fluid within the chamber 64 magnifies the effect of the mirror rotation on the deflection of the emerging focused wave field.

In FIG. 2 is shown that the vibrating mirror 71 may be designed as to be rotated about a horizontal axis 76 coincident or parallel to the main axis 75. Driving means such as an electric motor and a gear and/or lever system are not illustrated in FIG. 2. Rotation may also be about a horizontal axis lying within the mirror 71, as will be illustrated in FIG. 3, or about a vertical axis, as will be illustrated in FIG. 4. Due to the aforementioned magnifying effect, which is based on different indices of refraction, only small deflections are required. This leads to a very compact system.

For breast imaging, close proximity to the patient is facilitated by sloping the top 77 of the transmitting unit 42 and by sloping the bottom 79 of the receiving unit 44 to accommodate the patient's upper and lower body portions. The ultrasonic mirrors 50 and 71 are provided at the interior of these sloped surfaces to redirect the ultrasonic waves at approximately right angles to waves traversing the tissues in the examination space 14.

In FIG. 2 the scan direction is across the breast medial-lateral, and vice-versa.

Figure 4:
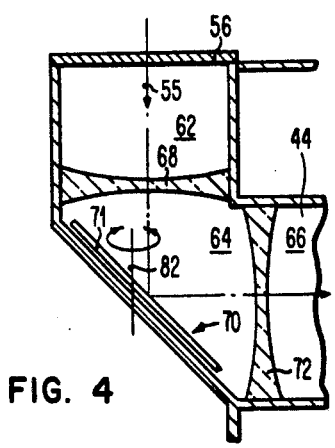
FIG. 4 is a partial cross-sectional view of still another ultrasound scanning device used in the imaging system according to FIG. 2.
Figure 3:
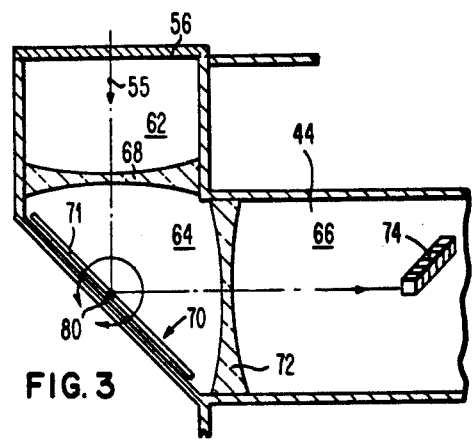
FIG. 3 is a partial cross-sectional view of another scanning device, applicable in an ultrasonic transmission imaging system according to this invention.

Instead of the mirror scanning device 70 illustrated in FIGS. 2 to 4 other scanning devices such as rotating prisms may also be used for scanning the image. The mirror scanning design, however, has the advantage that it is specifically compact and yields only few spurious reverberations.

In FIG. 3 is illustrated that the mirror 70 may perform rocking motions about a horizontal axis 80 lying in the plane of the mirror 71 to provide full scanning coverage of the breast. In this case, the detector array 74 is oriented perpendicular to the plane of the drawing. This is indicated in FIG. 3 by a perspective view of the receiving transducer array 74. In FIG. 3 the scan direction is along the breast dorsal-to-ventral, and vice-versa.

According to FIG. 4, the vibrating or rocking mirror 71 is again arranged in the chamber 64. In its resting position it is located at approximately 45° with respect to the main axis 55 of the ultrasound in the examination gap 14. In this embodiment the scanning mirror 71 can be rotated about a vertical axis 82. The rocking means for driving the mirror 71 may be arranged at a suitable position outside the chamber 64. This embodiment requires only comparatively little energy to move the fluid in the chamber 64. The scanning device 70 provides a medial-to-lateral scan of the breast.

The present invention combines convenience in coupling ultrasonic waves to a patient when, for example, imaging the breast, and provides a simple device 70 for scanning. If a rocking mirror 71 is utilized to scan the image rather than rotating the prisms, there is achieved a considerable design simplicity, few spurious reverberations and convenience in allowing room for a seated patient to be in close proximity to the apparatus.

For breast imaging, the present apparatus design insures imaging close to the chest wall and provides compression of the breast for enhanced image quality. The apparatus is particularly suitable for breast screening, for instance, on a routine basis, and other applications in which a series of images must be produced quickly, and without time consuming preparations.

While the forms of the compact ultrasonic apparatus for medical examinations herein described constitute preferred embodiments of the invention, it is to be understood that the invention is not limited to these precise forms of assembly, and that a variety of changes may be made therein without departing from the scope of the invention.

What is claimed is:

1. An ultrasound apparatus for medical examination of a patient's breast; comprising in combination:
    (a) an ultrasonic wave-generating transducer for providing ultrasonic waves;
    (b) a first horizontal ultrasound window;
    (c) first guiding means containing a fluid medium for guiding said ultrasonic waves to said first horizontal ultrasound window;
    (d) a second horizontal ultrasound window;
    (e) each of said first and second ultrasound windows defining an examination gap for introducing and insonifying the patient's breast positioned therein with ultrasonic waves having a vertical main axis;
    (f) an ultrasonic receiving transducer for converting at least a portion of an acoustic image field received from said gap to electrical signals;
    (g) second guiding means containing a fluid medium for guiding ultrasound transmitted through said gap from said second ultrasound window to said ultrasound receiving transducer;
    (h) lens means associated with said second guiding means for focusing said acoustic image field from said gap at said ultrasonic receiving transducer and for forming an image of the patient's breast thereon; and
    (i) a rocking mirror associated with said second guiding means for deflecting ultrasound energy passing through said gap towards said receiving transducer in a direction which is different from said main insonification direction in said gap, wherein said rocking mirror is movable about a rotation axis for sweeping said acoustic image field across said receiving transducer.

2. The ultrasound apparatus according to claim 1, wherein the width of said gap is adjustable in said main insonification direction.

3. The ultrasound apparatus according to claim 2, further comprising means for retaining said second window in a fixed position, and means for moving said first window with respect to said second window, thereby adjusting said gap.

4. The ultrasound apparatus according to claim 1, wherein said first and second windows are formed by rigid ultrasound transmitting plates.

5. The ultrasound apparatus according to claim 1, wherein said rocking mirror is positioned in the ultrasonic path between a first and a second imaging lens.

6. The ultrasound apparatus according to claim 5, wherein said rocking mirror is positioned at an angle of 45° with respect to the vertical main axis of said ultrasound waves received from said second window.

7. The ultrasound apparatus according to claim 1, wherein a housing is provided for forming said first and second guiding means, and wherein recesses are provided in said housing for receiving portions of the patient not under examination.

8. The ultrasound apparatus according to claim 7, further comprising rotating means for rotating said housing about a horizontal axis of said examination gap.

9. The ultrasound apparatus according to claim 1, wherein said rotation axis of said rocking mirror is arranged horizontally.

10. An ultrasound apparatus for medical examination of a patient's breast; comprising in combination:
(a) an ultrasonic wave-generating transducer for providing ultrasonic waves;
(b) a first horizontal ultrasound window;
(c) first guiding means containing a fluid medium for guiding said ultrasonic waves to said first horizontal ultrasound window;
(d) a second horizontal ultrasound window;
(e) each of said first and second ultrasound windows defining an examination gap for introducing and insonifying the patient's breast positioned therein with ultrasonic waves having a vertical main axis;
(f) an ultrasonic receiving transducer for converting at least a portion of an acoustic image field received from said gap to electrical signals;
(g) second guiding means containing a fluid medium for guiding ultrasound transmitted through said gap from said second ultrasound window to said ultrasound receiving transducer;
(h) lens means associated with said second guiding means for focusing said acoustic image field from said gap at said ultrasonic receiving transducer and for forming an image of the patient's breast thereon; and
(i) a rocking mirror associated with said second guiding means for deflecting ultrasound energy passing through said gap towards said receiving transducer in a direction which is different from said main insonification direction in said gap wherein said rocking mirror is movable about a rotation axis for sweeping said acoustic image field across said receiving transducer;
wherein said ultrasound windows further comprising resilient pads for engaging the patient's breast.

11. An ultrasound apparatus for medical examination of a patient's breast; comprising in combination:
(a) an ultrasonic wave-generating transducer for providing ultrasonic waves;
(b) a first horizontal ultrasound window;
(c) first guiding means containing a fluid medium for guiding said ultrasonic waves to said first horizontal ultrasound window;
(d) a second horizontal ultrasound window;
(e) each of said first and second ultrasound windows defining an examination gap for introducing and insonifying the patient's breast positioned therein with ultrasonic waves having a vertical main axis;
(f) an ultrasonic receiving transducer for converting at least a portion of an acoustic image field received from said gap to electrical signals;
(g) second guiding means containing a fluid medium for guiding ultrasound transmitted through said gap from said second ultrasound window to said ultrasound receiving transducer;
(h) lens means associated with said second guiding means for focusing said acoustic image field from said gap at said ultrasonic receiving transducer and for forming an image of the patient's breast thereon;
(i) a rocking mirror associated with said second guiding means for deflecting ultrasound energy passing through said gap towards said receiving transducer in a direction which is different from said main insonification direction in said gap wherein said rocking mirror is movable about a rotation axis for sweeping said acoustic image field across said receiving transducer; and
(j) a mirror for deflecting ultrasonic waves from said ultrasonic wave-generating transducer towards said first window.

12. The ultrasound apparatus according to claim 11, wherein said first mirror is positioned at an angle of 45° with respect to the main axis of said ultrasonic waves.

13. An ultrasound apparatus for medical examination of a patient's breast; comprising in combination:
(a) an ultrasonic wave-generating transducer for providing ultrasonic waves;
(b) a first horizontal ultrasound window;
(c) first guiding means containing a fluid medium for guiding said ultrasonic waves to said first horizontal ultrasound window;
(d) a second horizontal ultrasound window;
(e) each of said first and second ultrasound windows defining an examination gap for introducing and insonifying the patient's breast positioned therein with ultrasonic waves having a vertical main axis;
(f) an ultrasonic receiving transducer for converting at least a portion of an acoustic image field received from said gap to electrical signals;
(g) second guiding means containing a fluid medium for guiding ultrasound transmitted through said gap from said second ultrasound window to said ultrasound receiving transducer;
(h) lens means associated with said second guiding means for focusing said acoustic image field from said gap at said ultrasonic receiving transducer and for forming an image of the patient's breast thereon; and
(i) a rocking mirror associated with said second guiding means for deflecting ultrasound energy passing through said gap towards said receiving transducer in a direction which is different from said main insonification direction in said gap wherein said rocking mirror is movable about a rotation axis for sweeping said acoustic image field across said receiving transducer;
wherein said second guiding means further comprising a compartment containing a liquid having an ultrasound velocity which is lower than that of water.

14. The ultrasound apparatus according to claim 13, wherein said liquid is a fluoridated hydrocarbon.

* * * * *